United States Patent [19]

Yamada et al.

[11] 4,005,075

[45] Jan. 25, 1977

[54] PENICILLINS AND THEIR PREPARATION

[75] Inventors: Hirotada Yamada, Nishinomiya; Hisao Tobiki, Toyonaka; Iwao Nakatsuka, Nishinomiya; Norihiko Tanno; Kozo Shimago, both of Takarazuka; Takenari Nakagome, Nishinomiya, all of Japan

[73] Assignee: Sumitomo Chemical Company, Limited, Japan

[22] Filed: Sept. 5, 1975

[21] Appl. No.: 610,754

Related U.S. Application Data

[62] Division of Ser. No. 458,417, April 5, 1974, Pat. No. 3,945,995.

[30] Foreign Application Priority Data

Apr. 5, 1973 Japan ............... 48-39358

[52] U.S. Cl. .............. 260/239.1; 424/271
[51] Int. Cl.² ................ C07D 499/68
[58] Field of Search ................ 260/239.1

[56] References Cited

UNITED STATES PATENTS

| | | | |
|---|---|---|---|
| 3,433,784 | 3/1969 | Long et al. | 260/239.1 |
| 3,741,960 | 6/1973 | Alburn et al. | 260/239.1 |
| 3,804,820 | 4/1974 | Quitt et al. | 260/239.1 |
| 3,864,329 | 2/1975 | Tobiki et al. | 260/239.1 |

*Primary Examiner*—Gerald A. Schwartz
*Attorney, Agent, or Firm*—Stewart and Kolasch, Ltd.

[57] ABSTRACT

Penicillins of the formula:

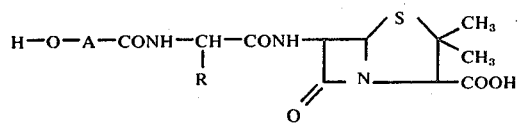

wherein R is an unsubstituted phenyl group or a substituted phenyl group having one or more hydroxyl groups or a cyclohexadienyl group and A represents a monocyclic or polycyclic nitrogen-containing heterocyclic aromatic ring, which are useful as antimicrobial agents having a broad antimicrobial spectrum against gram-positive and gram-negative bacteria including Pseudomonas and can be produced advantageously from the phenacyl ester of 6-aminopenicillanic acid through a series of steps.

4 Claims, No Drawings

PENICILLINS AND THEIR PREPARATION

This application is a divisional, of copending application Ser. No. 458,417, filed on Apr. 5, 1974 now U.S. Pat. No. 3,945,995.

The present invention relates to penicillins and their preparation. More particularly, it relates to penicillins and their non-toxic, pharmaceutically acceptable salts, which are useful as antimicrobial agents having a broad antimicrobial spectrum including Pseudomonas, and their preparation.

It is well known that penicillin antibiotics generally inhibit the growth of various gram-positive and gram-negative bacteria and are effective in treatment of infections with these bacteria. However, most of them do not exert any appreciable antimicrobial activity against Pseudomonas. Thus, only a few show a broad antimicrobial spectrum against a variety of gram-positive and gram-negative bacteria including Pseudomonas. On the other hand, there is a tendency that the infections caused by Pseudomonas are increasing. Recently, some penicillin antibiotics effective in treatment of the infections with Pseudomonas such as "Carbenicillin" and "Sulfocillin" appeared on the market, but their anti-Pseudomonas activity is not sufficiently strong.

In U.S. Pat. No. 3,433,784, there are described some N-acyl derivatives of aminobenzylpenicillin (ampicillin) as showing a minimal inhibitory concentration of 125 to 250 μg/ml against Pseudomonas pyocinea A or R 59, when determined by the standard test method. The anti-Pseudomonas activity of the compounds as described in the working examples is, however, not so high and the antimicrobial activity against other gram-negative bacteria is considerably low. Thus, it may be said that the N-acyl derivatives of ampicillin are less valuable than ampicillin itself from the practical viewpoint.

As the result of the study seeking penicillins which have a broad antimicrobial spectrum and are highly active against gram-positive and gram-negative bacteria including Pseudomonas, it has been found that, among various compounds, the penicillins of the following formula characteristically show a noticeable antimicrobial activity against Pseudomonas and a broad antimicrobial spectrum without exerting any serious side effect:

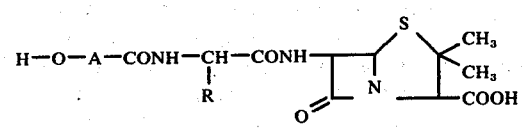
(I)

wherein R is a phenyl group bearing or not one or more hydroxyl groups or a cyclohexadienyl group and A represents a monocyclic or polycyclic nitrogen-containing heterocyclic aromatic ring.

Accordingly, a main object of the present invention is to provide the penicillins (I) and their non-toxic salts which are useful as antimicrobial agents. Another object of this invention is to provide a process for preparing the penicillins (I) and their non-toxic salts. A further object of the invention is to provide a use of the penicillins (I) and their non-toxic salts as antimicrobial agents. These and other objects of the invention will be apparent to those conversant with the art from the foregoing and subsequent descriptions.

The penicillins (I) of the invention are characteristic in that the heterocyclic aromatic ring represented by the symbol A bears at least one hydroxyl group, preferably at the position adjacent to the carbon atom to which the 6-(α-aminoacylamido)penicillanic acid moiety of the formula:

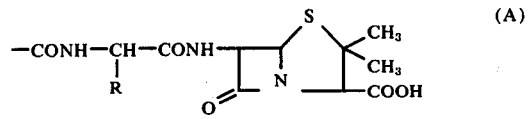
(A)

wherein R is as defined above is linked. In case of the hydroxyl group being capable of taking a tautomeric form such as a keto-enol form, it may be present in a keto form (O=C<). The compounds wherein the said heterocyclic aromatic ring bears no such substituent are antimicrobially much less active than those bearing the substituent and exhibit only the same low antimicrobial activity as those disclosed in U.S. Pat. No. 3,433,784 against Pseudomonas as well as other gram-negative bacteria.

The heterocyclic aromatic ring represented by the symbol A should include at least one six-membered ring unit. Examples of the heterocyclic aromatic ring are pyridine, pyrimidine, pyridazine, triazine, pyrazine, quinoline, isoquinoline, cinnoline, naphthyridine, quinoxaline, pyrazolopyridine, thiazolopyrimidine, pyridopyrimidine, etc.

The said heterocyclic aromatic ring may bear, in addition to at least one hydroxyl group as stated above, any other substituent(s), of which examples are as follows: lower alkyl, lower alkoxy, lower alkanoyl, lower alkoxycarbonyl, lower alkylthio, mercapto, lower alkoxymethyl, halogen, cyano, nitro, lower alkylsulfonyl, arylsulfonyl, sulfamoyl, carbamoyl, aryloxycarbonylamino, acetoacetylamino, lower alkylamino, di(-lower)alkylamino, halo(lower)alkyl, lower alkenyl, aryl, cyclo(lower)alkyl, condensed cyclo(lower)alkylene, etc.

The non-toxic, pharmaceutically acceptable salts of the penicillins (I) are, for instance, the inorganic salts such as sodium, potassium ammonium, calcium and magnesium salts and the organic salts such as diethylamine, triethylamine, N,N'-dibenzylethylenediamine, diethanolamine, pyrrolidine, morpholine and procaine salts.

According to the present invention, the penicillins (I) can be produced from the phenacyl ester of 6-aminopenicillanic acid through the steps as shown in the following scheme:

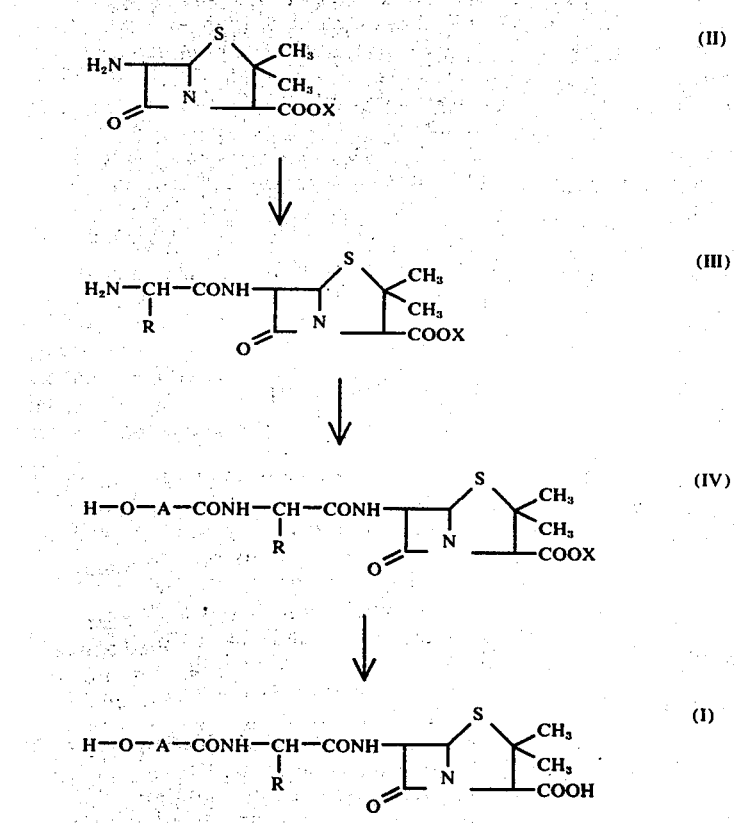

(II)

(III)

(IV)

(I)

wherein X is a phenacyl group which may optionally bear any substituent such as halogen, nitro or lower alkoxy on the benzene ring and R is as defined above.

That is, the phenacyl 6-aminopenicillanate (II), which may be in the free or salt form, is first reacted with a carboxylic acid of the formula:

  (V)

wherein R' and R'' are each a hydrogen atom or an amino protective group and R is as defined above or its reactive derivative to give a phenacyl 6-(α-aminoacylamido)penicillanate of the formula:

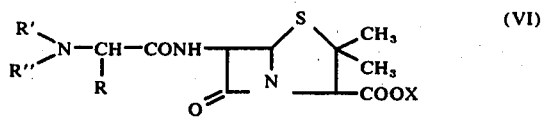  (VI)

wherein R, R', R'' and X are each as defined above.

The reaction can be carried out in a conventional coupling method and/or by the use of a conventional coupling reagent in the related art field, i.e. in the synthesis of peptides, penicillins, cephalosporins and the like.

This, the reaction is usually carried out in an inert solvent (e.g. dichloromethane, chloroform, acetone, dimethylformamide, tetrahydrofuran, dioxane, acetonitrile, methlisobutylketone, toluene). The reactive derivative of the carboxylic acid (V) may be any form being capable of acting as an acylating agent. Specific examples are the acid halide, acid azide, acid anhydride, mixed anhydride, active amide, active ester, active thioester, etc. When the carboxylic acid (V) is used in the free form, the reaction is normally effected in the presence of an enzyme, a carbodiimide reagent (e.g. N,N'-dicyclohexylcarbodiimide), an isoxazolium salt (e.g. Woodward reagent) or the like.

In case of both R' and R'' being hydrogen, the carboxylic acid (V) is favorably employed in the form of a salt (e.g. hydrochloride). As the amino protective group, there may be used any conventional one. When, for instance, R' is a hydrogen atom, R'' may represent carbonylvinyl (Japanese Pat. Publications Nos. 15947/1967, 28189/1970 and 41554/1971; Angewandte Chemie, 76, 342), o-nitrophenylthio (Japanese Pat. Publications Nos. 11073/1967 and 22589/1972), p-toluenesulfonylethoxycarbonyl (Japanese Pat. Publication No. 17193/1968), carbobenzyloxy (Japanese Pat. Publication No. 16277/1961) or the like. Further, R' and R'' may form a Schiff base (Japanese Pat. Publication No. 24780/1965).

When the thus produced phenacyl 6-(α-aminoacylamido)penicillanate (VI) includes an amino protective group, it may be treated by a per se conventional procedure for cleavage of such amino protective group to give the corresponding phenacyl 6-(α-aminoacylamido)penicillanate (III).

The phenacyl 6-(α-aminoacylamido)penicillanate (III) or its salt is then reacted with a carboxylic acid of the formula:

H—O—A—COOH    (VII)

wherein A is as defined above or its reactive derivative.

The reaction may be effected in substantially the same manner as that for the reaction between the phenacyl 6-aminopenicillanate (II) and the carboxylic acid (V). Thus, the reaction is ordinarily carried out in an inert solvent (e.g. dichloromethane, chloroform, acetone, dimethylformamide, tetrahydrofuran, dioxane, acetonitrile, methylisobutylketone, toluene). As the reactive derivative of the carboxylic acid (VII), there may be exemplified the acid halide, acid azide, acid anydride, mixed anhydride, active amide, active ester, active thioester, etc.

When the mixed anhydride is prepared for the activation of the carboxylic acid, the following procedure may be recommended. Thus, the carboxylic acid (VII) (1 mol) is reacted with about a 2 molar amount of a lower alkoxylcarbonyl halide (e.g. ethyl chloroformate, isobutyl chloroformate) or a lower alkanoyl halide (e.g. pivaloyl chloride) in the presence of about a 2 molar amount of a base to give a mixed anhydride of the formula:

Z—O—A—COOZ        (VIII)

wherein Z is an acyl group and A is as defined above.

The product in the amidation using such a mixed anhydride is the one representable by the formula:

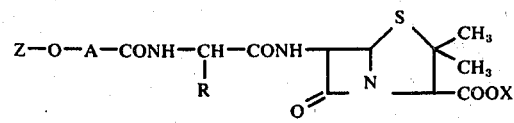

wherein A, R, X and Z are each as defined above, which may be treated with an organic or inorganic base (e.g. sodium carbonate, potassium carbonate, sodium hydroxide, ammonia water, triethylamine, dimethylamine, potassium 2-ethylhexanoate) to give the corresponding penicillin phenacyl ester (VI).

Alternatively, the elimination of the group Z in the phenacyl 6-(α-acylamidoacylamido)penicillanate (IX) may be accomplished simultaneously with the elimination of the phenacyl group in the subsequent step as hereinafter illustrated.

When the carboxylic acid (VII) is in the form of a keto-enol tautomer and the carboxyl group and the hydroxyl group are present at the positions adjacent to each other, it may be reacted with an equimolar amount of phosgene in the presence of about twice the molar amount of an acid eliminating agent to give an inner molecular acid anhydride of the formula:

wherein A is as defined above. The use of thionyl chloride, phosphorous trichloride or the like in place of phosgene affords the similar type of inner molecular acid anhydride. These inner molecular acid anhydrides can be subjected to amidation in the same manner as above.

The phenacyl 6-(α-acylamidonacylamido)penicillanate (IV) is then subjected to treatment for splitting off the phenacyl group. The treatment is usually carried out with a base in an inert solvent (eg. dimethylformamide, dimethylacetamide, dimethylsulfoxide, sulfolane, hexamethyl phosphoric triamide, acetone, acetonitrile, dioxane, tetrahydrofuran, ethanol, isopropanol, water), preferably at room temperature or any lower temperature. As the base, there may be employed, for instance, sodium thiophenoxide, sodium thio-p-chlorophenoxide, sodium thiomethoxide, sodium thioethoxide, sodium thiopropoxide, sodium thioisopropoxide, sodium thiobutoxide, sodium thioisobutoxide, sodium thio-tert.-butoxide, sodium hydroxide, potassium hydroxide, sodium hydrogen sulfide, etc. Among them, the use of sodium thiophenoxide, sodium thio-p-chlorophenoxide or sodium thioalkoxide is favorable. The molar ratio of the phenacyl 6-(α-acylamidoacylamido)penicillanate (IV) and the base may be normally 1 : 1 – 3.

As the result, there is usually obtained the penicillin (I) in the form of a salt, which may be treated with an acid to convert it into a free form.

The starting phenacyl 6-aminopenicillanate (II) may be produced, for instance, by reacting benzylpenicillin phenacyl ester (prepared by the procedure as described in U.S. Pat. No. 2,650,218) with a phosphorus halide, reacting the resultant iminohalide with a lower alkanol and hydrolyzing the resulting iminoether.

These conversions may be represented by the following formulae:

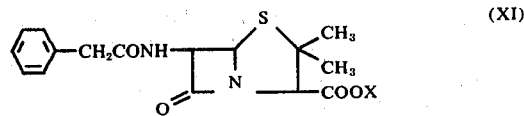

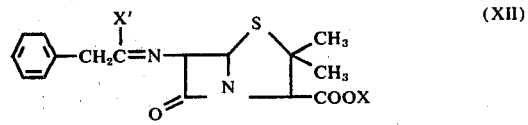

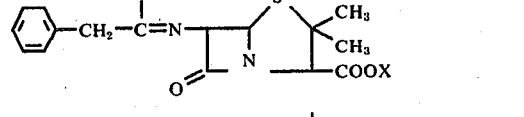

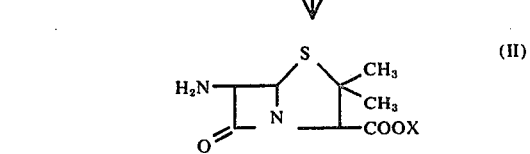

wherein X' is a halogen atom, R''' is a lower alkoxy group and X is as defined above.

The reaction of the benzylpenicillin phenacyl ester (XI) with a phosphorus halide (e.g. phosphorous pentachloride, phosphorus pentabromide, phosphorus oxychloride, phosphorus trichloride) is carried out in the presence of an acid eliminating agent (e.g. N-methylmorpholine, pyridine, N,N-dimethylaniline, triethylamine) in an inert solvent (e.g. chloroform, dichloroethane, dichloromethane, trichloroethylene, toluene), preferably at a temperature from 0 to −50° C. The acid eliminating agent is usually employed in an amount of about 3 to 5 mol to 1 mol of the phosphorus halide.

The reaction of the resultant iminohalide with a lower alkanol is preferably carried out in the presence of an acid eliminating agent (e.g. N-methylmorpholine) at a temperature from 0 to −50° C. An alkaline earth metal carbonate may be added. Examples of the lower alkanol are methanol, ethanol, n-propanol, n-butanol, etc.

The hydrolysis of the resulting iminoether (XIII) is performed in the presence of a base. For instance, the iminoether (XIII) is admixed with water, preferably a dilute aqueous solution of alkali (e.g. sodium hydroxide, ammonia), the resultant mixture is adjusted pH 4 to 7 and stirring is effected while cooling with ice. From the reaction mixture, the organic solvent layer is separated and dilute hydrochloric acid is added thereto, followed by stirring under cooling with ice to precipitate the hydrochloride of the phenacyl 6-aminopenicillanate (II). Alternatively, the organic solvent layer separated from the reaction mixture may be admixed with an acid such as p-toluenesulfonic acid to give the corresponding acid salt.

The thus prepared salt has a high purity and any further purification is usually not needed.

The process for preparation of the penicillins (I) according to the present invention as illustrated above is characteristic in the use of the phenacyl 6-aminopenicillanate (II) as the starting material. By the use of such phenacyl ester, the penicillins (I) can be advantageously produced in a good yield with a high purity by simple operations.

Throughout the specification, the term lower alkyl is intended to mean generally both straight and branched chain aliphatic hydrocarbon groups having not more than eight carbon atoms (preferably not more than five carbon atoms) such as methyl, ethyl, propyl, isopropyl, butyl, isobutyl, amyl and isoamyl. Similarly where the term lower is used as a part of the description of any other group (e.g. lower alkoxy, lower alkylthio, halo(lower)alkyl, lower alkylamino, di(lower)alkylamino), it usually refers to the alkyl portion of such group. The halogen atom includes chloride, bromine, iodine and fluorine.

Practical and presently preferred embodiments of the invention are illustratively shown in the following Examples.

EXAMPLE A

Preparation of phenacyl 6-aminopenicillanate:

To a mixture of benzylpenicillin phenacyl ester (18.1 g), N-methylmorpholine (8.96 ml) and dichloromethane (200 ml) cooled at −25° C, phosphorus pentoxide (9.60 g) was portionwise added in 5 minutes, and stirring was continued at −18° to −10° C for 30 minutes. After cooling the resultant mixture to −25° C, a mixture of methanol (320 ml) and N-methylmorpholine (8.96 ml) was dropwise added thereto over a period of 5 minutes, and stirring was continued at −17° to −°10° C for 2 hours. The reaction mixture was cooled with ice and poured onto a saturated aqueous solution of sodium chloride (640 ml), and the resultant mixture was adjusted to pH 6.0 to 6.5 with N sodium hydroxide solution. The water layer was separated from the dichloromethane layer and extracted with ethyl acetate (500 ml). The ethyl acetate extract was combined with the dichloromethane layer, washed with sodium bicarbonate solution and a saturated aqueous solution of sodium chloride in order and dried over anhydrous magnesium sulfate. After cooling with ice, 2 N hydrochloric acid (20ml) was added thereto whereby white crystals were precipitated. The precipitated crystals were collected by filtration, washed with ethyl acetate and ether in order and dried over anhydrous phosphorus pentoxide to give phenacyl 6-aminopenicillanate hydrochloride (7.84 g). M.P. 155° to 157° C (decomp.).

When a solution of p-toluenesulfonic acid monohydrate in acetone was added to the organic solvent layer as above mentioned, ether was added thereto until turbidity was produced and the resultant mixture was allowed to stand in a refrigerator overnight, there was produced phenacyl 6-aminopenicillanate p-toluenesulfonate. M.P. 132° C (decomp.).

EXAMPLE B

Preparation of p-bromophenacyl 6-aminopenicillanate:

As in Example A, there was produced the objective compound in the form of the hydrochloride (2.1 g; M.P. 150° to 156° C (decomp.)) from benzylpenicillin p-bromophenacyl ester (5.31 g).

EXAMPLE C

Preparation of p-nitrophenacyl 6-aminopenicillanate:

As in Example A, there was produced the objective compound in the form of the benzenesulfonate (2.9 g) from p-nitrophenacyl benzylpenicillin p-nitrophenacyl ester (4.97 g).

EXAMPLE D

Preparation of p-methoxyphenacyl 6-aminopenicillanate:

As in Example A, there was produced the objective compound in the form of the benzenesulfonate (2.7 g) from benzylpenicillin p-methoxyphenacyl ester (4.80 g).

EXAMPLE E (1) Preparation of 4-hydroxy-1,5-naphthyridine-3-carbonyl chloride hydrochloride:

To a mixture of dimethylformamide (0.73 g) and thionyl chloride (1.56 g) in benzene, there was added dropwise 4-hydroxy-1,5-naphthyridine-3-carboxylic acid (1.9 g) while stirring, and the reaction was carried out at 40° to 85° C for 3 hours. The crystals were collected by filtration, washed with benzene and dried under reduced pressure to give the objective compound (2.37 g). Purity, 96.3%. M.P. <350° C.

(2) Preparation of 4-hydroxy-1,5-naphthyridine-3-carboxylic acid N-succinimide ester:

To a mixture of N-hydroxysuccinimide (22.2 g), triethylamine (35.5 g) and dimethylformamide (800 ml), the carbonyl chloride hydrochloride as prepared in (1) (43.2 g) was protionwise added, and the resultant mixture was gradually heated and stirred at 60° C for 30 minutes. After the addition of triethylamine (1.77 g), stirring was continued at the same temperature as above for 1 hour. The reaction mixture was cooled to about 30° C, and the crystals were collected by filtration and washed with dichloromethane and acetone in order to give the objective compound (34.2 g). M.P. 310° to 311° C (decomp.).

EXAMPLE F

Preparation of p-nitrophenyl 3-hydroxypyridazine-4-carboxylate:

3-Hydroxypyridazine-4-carboxylic acid (1.40 g) was dissolved in pyridine (20 ml) at 40° C, and p-nitrophenyl trifluoroacetate (2.82 g) was dropwise added thereto. The resultant mixture was stirred at 40° to 50° C for 1 hour and concentrated under reduced pressure to dryness. The residue was washed with chloroform and acetone in order and dried to give the objective compound (2.21 g). M.P. 233° C (decomp.).

EXAMPLE 1

(a) Preparation of 6D-α-aminobenzylpenicillin phenacyl ester:

To a suspension of phenacyl 6-aminopenicillanate hydrochloride prepared as in Example A (1.85 g) and D-phenylglycyl chloride hydrochloride (1.29 g) in dichloromethane (20 ml), sodium bicarbonate (1.05 g) was added, and the resultant mixture was stirred while cooling with ice for 6 hours. The reaction mixture was filtered to eliminate the by-produced sodium chloride. The filtrate was admixed with isopropanol and concentrated under reduced pressure by the aid of a rotary evaporator. After the evaporation of dichloromethane, the precipitate was collected by filtration to give the objective compound in the form of the hydrochloride (2.19 g). M.P. 142° to 148° C (decomp.).

(b) preparation of D-α-(4-hydroxy-1,5-naphthyridine-3-carbonamido)benzylpenicillin:

To a solution of 6-D-α-aminobenzylpenicillin phenacyl ester (hydrochloride) (2.01 g) and triethylamine (0.808 g) in dimethylformamide (20 ml), 4-hydroxy-1,5-naphthyridine-3-carboxylic acid N-succinimide ester (M.P. 310° to 311° C (decomp.)) (1.15 g) was added while cooling with ice, and the resultant mixture was stirred for 1 hour. Stirring was further continued at room temperature for 2 hours. After cooling with ice, 1% sodium bicarbonate solution (100 ml) was added thereto. The precipitated crystals were collected by filtration, washed with water and dried over phosphorus pentoxide to give D-(α-4-hydroxy-1,5-naphthyridine-3-carboxamido)benzylpenicillin phenacyl ester (2.17 g).

The above product was dissolved in dimethylformamide (65 ml), sodium thiophenoxide (0.89 g) was added thereto, and the resultant mixture was stirred at room temperature for 1 hour. To the resultant mixture, acetone (650 ml) was added, and the separated crystals were collected by filtration and washed with acetone and ether in order to give the objective compound in the form of the sodium salt (1.3 g).

In the above procedure, the use of 4-hydroxy-1,5-naphthyridine-3-carbonyl chloride in place of 4-hydroxy-1,5-naphthyridine-3-carboxylic acid N-succinimide ester can also afford the same objective compound as above. The use of sodium thio-n-propoxide in place of sodium thiophenoxide can also give the objective compound in the form of the sodium salt.

EXAMPLE 2

(a) Preparation of phenacyl 6-(D-α-amino-p-hydroxy-phenylacetamido)penicillanate:

To a suspension of pulverized sodium N-(2-methoxycarbonyl-1-methylvinyl)-D-α-amino-p-hydroxyphenylacetate (2.87 g) in ethyl acetate (40 ml), several drops of N-methylmorpholine were added, and the resulting mixture was cooled to −15° C. Ethyl chloroformate (1.0 ml) was added thereto while stirring, and stirring was continued at −10° C for 30 minutes. The resulting mixture was cooled to −25° C, and the by-produced sodium chloride was eliminated by filtration. The filtrate was cooled to −10° C, and a solution of phenacyl 6-aminopenicillanate (3.34 g) in ethyl aetate (20 ml) was dropwise added thereto. The resulting mixture was stirred for 10 minutes at the same temperature as above and then for 50 minutes at room temperature. The reaction mixture was washed with water, sodium bicarbonate solution and water in order. The ethyl acetate layer was stirred under cooling with ice, N hydrochloric acid (10 ml) was added thereto, and stirring was continued for 40 minutes. After the addition of petroleum ether (20 ml), the resultant mixture was allowed to stand. The water layer was separated from the organic solvent layer, the organic solvent layer was extracted with water, and the water extract was combined with the said water layer. The thus obtained water solution was saturated with sodium chloride and the resulting yellowish organic layer was separated. The water layer was extracted with ethyl acetate-isopropanol and the extract was combined with the said yellowish organic layer. The resulting mixture was dried over anhydrous magnesium sulfate and concentrated under reduced pressure. The precipitated crystals were collected by filtration and dried under reduced pressure to give the objective compound in the form of the hydrochloride (3.1 g). M.P. 145° to 165° C (decomp.).

(b) Preparation of D-α-(4-hydroxy-1,5-naphthyridine-3-carbonamido)-p-hydroxy-phenylacetamidopenicillanic acid:

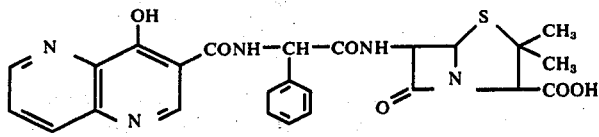

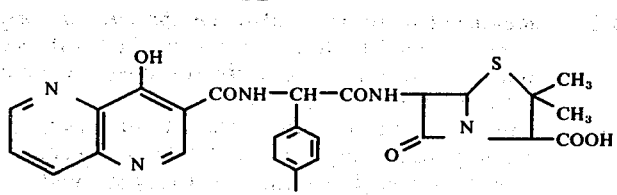

To a suspension of phenacyl 6-D-(α-amino-p-hydroxyphenylacetamido)penicillanate hydrochloride (5.19 g) in dimethylformamide (50 ml), triethylamine (2.02 g) was added, and stirring was carried out while cooling with ice. After the addition of 4-hydroxy-1,5-naphthyridine-3carboxylic acid N-succinimide ester (M.P. 310° to 311° C (decomp.)) (2.87 g) thereto, the resulting mixture was stirred while cooling with ice for 3 hours and then admixed with 2.5% sodium bicarbonate solution (300 ml), and the precipitated crystals were collected by filtration, washed with water and dried over phosphorus pentoxide to give phenacyl 6-D-α-(4-hydroxy-1,5-naphthyridine-3-carboxamido)-p-hydroxyphenylacetamidopenicillanate (6.0 g). This product was then treated as in Example 1 to give the objective compound in the form of the sodium salt (4.0 g).

EXAMPLE 3

Preparation of D-α-(4-hydroxypyridine-3-carbonamido)benzylpenicillin:

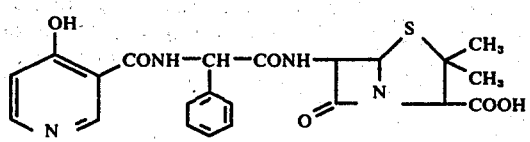

A solution of 4-hydroxynicotinic acid (1.39 g) and triethylamine (3.03 g) in dichloromethane (30 ml) was cooled to −20° C, a solution of isobutyl chloroformate (2.88 g) in dichloromethane (5 ml) was dropwise added thereto while stirring and the resultant mixture was stirred at the same temperature as above for 30 minutes. After the addition of 6-D-α-aminobenzylpenicillin phenacyl ester hydrochloride (5.03 g) thereto, the resultant mixture was stirred at the same temperature as above for 2 hours. The reaction mixture was concentrated under reduced pressure, and the residue was suspended in 2.5% sodium bicarbonate solution (30 ml). The crystals were collected by filtration, washed with water and dried over phosphorus pentoxide to give the phenacyl ester (5.1 g). This product was then treated as in Example 1 to give the objective compound in the form of the sodium salt (3.2 g).

EXAMPLE 4

Preparation of D-α-(4-hydroxycinnoline-3-carbonamido)benzylpenicillin:

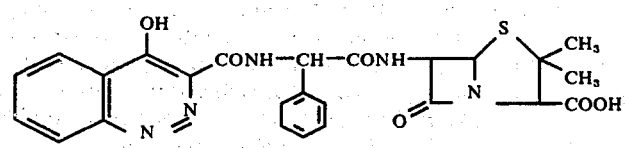

To a solution of 4-hydroxycinnoline-3carboxylic acid (1.90 g) in dimethylformamide (60 ml), carbonyldiimidazole (1.78 g) was added at room temperature while stirring. After 30 minutes, a solution of 6-D-α-aminobenzylpenicillin phenacyl ester (4.67 g) in dichloromethane (30 ml) was added thereto, and stirring was continued at the same temperature as above for 6 hours. The reaction mixture was admixed with 1% sodium bicarbonate solution (100 ml), and the precipitated crystals were collected by filtration and dried over phosphorus pentoxide under reduced pressure to give the phenacyl ester (4.5 g). This product was treated with sodium thiophenoxide as in Example 1 to give the objective compound in the form of the sodium salt.

EXAMPLE 5

Preparation of D-α-(3hydroxypyridazine-4-carbonamido)benzylpenicillin:

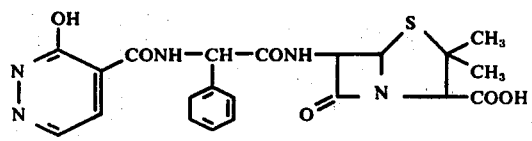

To a suspension of 6-D-α-aminobenzylpenicillin phenacyl ester hydrochloride (5.03 g) in dichloromethane (60 ml), triethylamine (2.02 g) and p-nitrophenyl 3-hydroxypyridazine-4-carboxylate (M.P. 233° C (decomp.)) (2.87 g) were added thereto at room temperature while stirring vigorously. After the addition of dimethylformamide (26 ml) thereto, stirring was continued for 4 hours. To the reaction mixture, 1% sodium bicarbonate solution (200 ml) was added, and the precipitated crystals were collected by filtration, washed with water and dried over phosphorus pentoxide under reduced pressure. The resulting product was treated as in Example 1 to give the objective compound in the form of the sodium salt (3.9 g).

EXAMPLE 6

(a) Preparation of phenacyl 6-[D-2-amino-2-(1,4-cyclohexadienyl)acetamido]penicillanate:

As in Example 2 (a), the objective compound in the form of the hydrochloride (3.3 g) was produced from sodium N-(2-methoxycarbonyl-1-methylvinyl)-D-α-amino-(1,4-cyclohexadienyl)acetate (2.73 g). As in Example 1 (a). the objective compound in the form of the hydrochloride (4.19 g) was produced from D-α-(4-cyclohexadienyl)glycyl chloride hydrochloride (2.08 g).

(b) Preparation of 6-[D-2-(4-hydroxy-1,5-naphthyridine-3-carbonamido-2-(1,4-cyclohexadienyl)acetamido]penicillanic acid:

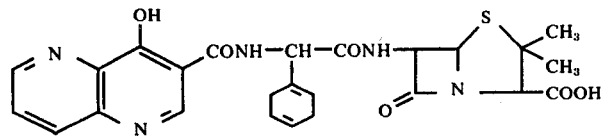

To a mixture of phenacyl 6-[D-2-amino-2-(1,4-cyclohexadienyl)acetamido]penicillanate hydrochloride (5.05 g), triethylamine (2.02 g) and dimethylformamide (50 ml), 4-hydroxy-1,5-naphthyridine-3-carboxylic acid N-succinimide ester (3.10 g) was added, and the reaction was carried out for 5 hours. The reaction mixture was cooled with ice, 1% sodium bicarbonate solution (200 ml) was added thereto, and the separated crystals were collected by filtration, washed with water and dried over phosphorus pentoxide. The resulting product was treated as in Example 1 to give the objective compound in the form of the sodium salt (4.6 g).

In the same manner as above, there are produced the compounds as shown in Table 1.

Table 1

| Example No. | R— | H—O—A— |
|---|---|---|
| 7 | phenyl | 4-hydroxy-2-hydroxypyrimidin-5-yl (OH at 4, HO at 2, methyl position) |
| 8 | phenyl | 4-hydroxypyrazin-3-yl |
| 9 | phenyl | 4-hydroxyquinolin-3-yl |
| 10 | phenyl | 3-hydroxypyridin-2-yl |
| 11 | phenyl | 2-hydroxypyridin-3-yl |
| 12 | phenyl | 4-hydroxy-5,6,7,8-tetrahydroquinolin-3-yl |
| 13 | phenyl | 6-methyl-2-hydroxypyridin-3-yl |
| 14 | 4-hydroxyphenyl | 6-dimethylamino-4-hydroxy-1,5-naphthyridin-3-yl |

4,005,075
Table 1-continued
| Example No. | R— | H—O—A— |
|---|---|---|
| 15 | 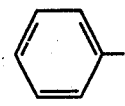 | 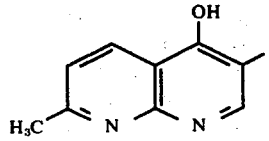 |
| 16 | 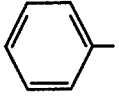 | 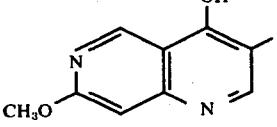 |
| 17 | 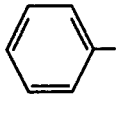 | 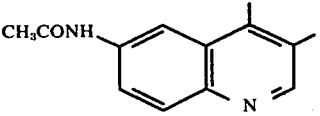 |
| 18 | 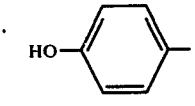 | 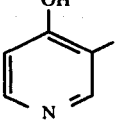 |
| 19 | 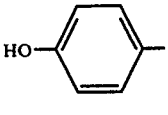 | 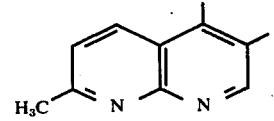 |
| 20 | 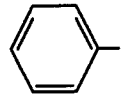 | 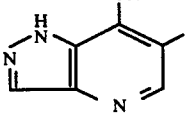 |
| 21 | 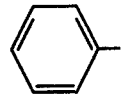 | 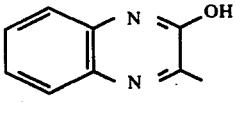 |
| 22 | 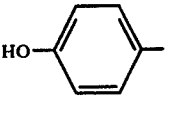 | 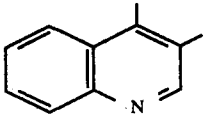 |
| 23 | 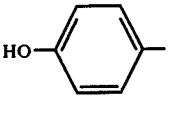 | 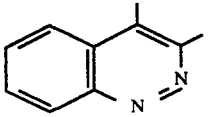 |
| 24 | 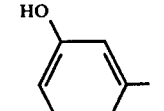 | 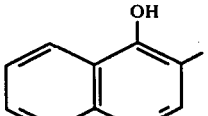 |
| 25 | 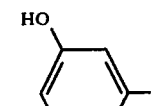 | 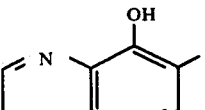 |

Table 1-continued

| Example No. | R— | H—O—A— |
|---|---|---|
| 26 | 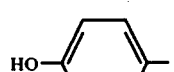 | 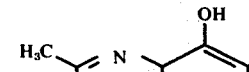 |
| 27 | 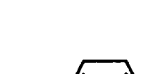 | 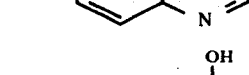 |
| 28 | 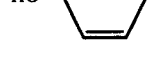 | 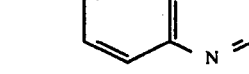 |

The antimicrobial activities of the compounds obtained in the above Examples determined by the standard test method (i.e. agar dilution method) as well as those of the following penicillins as disclosed in U.S. Pat. No. 3,433,784 are shown in Table 2:

Compound A

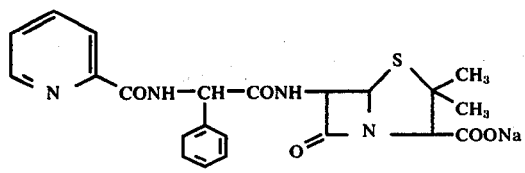

Compound B

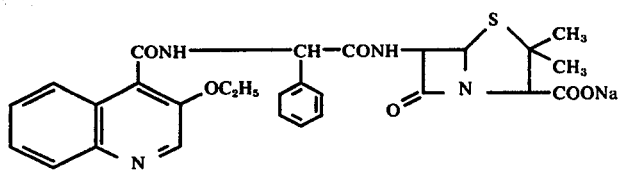

Table 2

| Example No. | Minimal inhibitory concentration (μg/ml) | | | | | |
|---|---|---|---|---|---|---|
| | Staphylococcus aureus 209P | Escherichia coli NIHJ | Proteus miravilis 2425 | Proteus vulgaris HX19 | Klebsiella pneumoniae 602 | Pseudomonas aeruginosa 104 |
| 1 | 0.78 | 1.56 | 3.13 | 0.1 | 6.25 | 1.56 |
| 2 | 1.56 | 0.78 | 1.56 | 0.0125 | 6.25 | 0.78 |
| 3 | 0.39 | 25 | 6.25 | 0.1 | 25 | 3.13 |
| 4 | 0.78 | 12.5 | 12.5 | 0.78 | 12.5 | 12.5 |
| 5 | 0.39 | 12.5 | 6.25 | 0.05 | 6.25 | 3.13 |
| 6 | 0.39 | 1.56 | 3.13 | <0.05 | 3.13 | 1.56 |
| 7 | 0.39 | 12.5 | 6.25 | 0.05 | 25 | 3.13 |
| 8 | 0.39 | 25 | 12.5 | 0.05 | 100 | 3.13 |
| 9 | 0.2 | 6.25 | 3.13 | 0.2 | 1.56 | 6.25 |
| 10 | 0.2 | 6.25 | 25 | 0.2 | 25 | 6.25 |
| 11 | 0.39 | 12.5 | 25 | 0.2 | 25 | 6.25 |
| 12 | 0.78 | 12.5 | 6.25 | (0.05) | 6.25 | 12.5 |
| 13 | 0.39 | 12.5 | 12.5 | 0.2 | 25 | 12.5 |
| 14 | 3.13 | 1.56 | 1.56 | 0.1 | 3.13 | 3.13 |
| 15 | 0.39 | 3.13 | 3.13 | 0.2 | 1.56 | 3.13 |
| 16 | 1.56 | 6.25 | 12.5 | 0.2 | 6.25 | 6.25 |
| 17 | 0.78 | 12.5 | 3.13 | (0.1) | 3.13 | 6.25 |
| 18 | 1.56 | 12.5 | 25 | 0.2 | 200 | 3.13 |
| 19 | 1.56 | 6.25 | 25 | 0.39 | 12.5 | 12.5 |
| 20 | 0.78 | 3.13 | 3.13 | 0.1 | 6.25 | 6.25 |
| 21 | 0.2 | 6.25 | 25 | 0.78 | 12.5 | 1.56 |
| 22 | 0.78 | 6.25 | 6.25 | 0.2 | 25 | 6.25 |
| 23 | 0.78 | 12.5 | 12.5 | 0.78 | 25 | 12.5 |
| 24 | 0.78 | 6.25 | 3.13 | 0.2 | 25 | 6.25 |
| 25 | 1.56 | 3.13 | 3.13 | 0.05 | 25 | 3.13 |

Table 2-continued

| Example No. | Minimal inhibitory concentration (μg/ml) | | | | | |
|---|---|---|---|---|---|---|
| | Staphylococcus aureus 209P | Escherichia coli NIHJ | Proteus miravilis 2425 | Proteus vulgaris HX19 | Klebsiella pneumoniae 602 | Psudomonas aeruginosa 104 |
| 26 | 0.78 | 1.56 | 1.56 | 0.05 | 12.5 | 1.56 |
| 27 | 0.78 | 3.13 | 3.13 | 0.05 | 12.5 | 3.13 |
| 28 | 0.78 | 1.56 | 1.56 | 0.05 | 6.25 | 3.13 |
| Compound A | 0.78 | 100 | 50 | 0.39 | 50 | 50 |
| Compound B | 0.39 | 50 | 100 | 12.5 | 25 | 100 |
| Carbenicillin | 0.78 | 12.5 | 0.78 | 0.78 | >200 | 50 |

What is claimed is:

1. A penicillin of the formula:

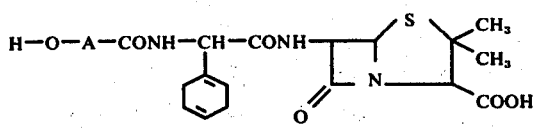

wherein A represents a heterocyclic aromatic ring selected from the group consisting of pyridine, pyrimidine, pyridazine, triazine, pyrazine, quinoline, isoquinoline, cinnoline, naphthyridine, quinoxaline, pyrazolopyridine, thiazolopyrimidine and pyridopyrimidine.

2. A penicillin of the formula:

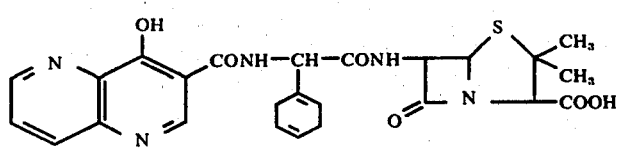

and non-toxic, pharmaceutically acceptable salts thereof.

3. A penicillin of the formula:

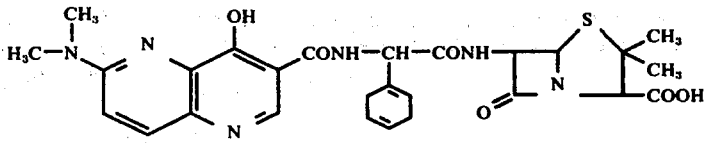

and non-toxic, pharmaceutically acceptable salts thereof.

4. A compound of the formula:

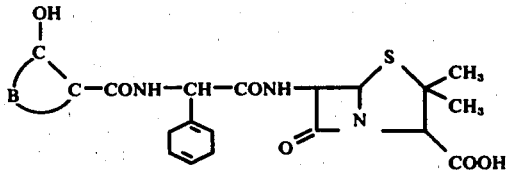

wherein

is a heterocyclic aromatic ring selected from the group consisting of pyridine, pyrimidine, pyridazine, triazine, pyrazine, quinoline, isoquinoline, cinnoline, naphthyridine, quinoxaline, pyrazolopyridine, thiazolopyrimidine and pyridopyrimidine.

* * * * *